US006540726B1

(12) United States Patent
Follman et al.

(10) Patent No.: US 6,540,726 B1
(45) Date of Patent: Apr. 1, 2003

(54) PERSONAL EYEWASH DELIVERY APPARATUS WITH INTEGRAL LEAKPROOF SEALING SYSTEM

(75) Inventors: Mark Follman, Glen Rock, NJ (US); Paul Thom, Montclair, NJ (US); David Landsberger, Caldwell, NJ (US)

(73) Assignee: Bel-Art Products, Inc., Pequannock, NJ (US)

( * ) Notice: Subject to any disclaimer, the term of this patent is extended or adjusted under 35 U.S.C. 154(b) by 0 days.

(21) Appl. No.: 09/563,653

(22) Filed: May 2, 2000

(51) Int. Cl.[7] .............................................. A61M 35/00
(52) U.S. Cl. ........................ 604/294; 604/295; 604/301
(58) Field of Search ................................ 604/294–301; 222/420; 215/232, 230, 256; 220/254

(56) References Cited

U.S. PATENT DOCUMENTS

| | | | | |
|---|---|---|---|---|
| 1,623,454 A | | 4/1927 | Wilson | |
| 1,692,143 A | | 11/1928 | Strunz | |
| 1,846,763 A | | 2/1932 | Schaefer | |
| D104,881 S | | 6/1937 | Rosengart | |
| 2,920,624 A | | 1/1960 | Lerner et al. | |
| 3,917,119 A | | 11/1975 | Kahn | |
| 5,295,981 A | * | 3/1994 | Smith et al. | 222/568 |
| 5,320,615 A | | 6/1994 | Van Keuren | |
| 5,387,202 A | | 2/1995 | Baron | |
| 5,588,564 A | * | 12/1996 | Hutson et al. | 222/383.1 |
| 5,904,259 A | * | 5/1999 | Hidding et al. | 215/230 |

FOREIGN PATENT DOCUMENTS

| | | | |
|---|---|---|---|
| DE | 3800499 | | 7/1989 |
| GB | 1515027 | | 10/1975 |
| GB | 2052453 A | | 1/1981 |
| GB | 2 052 453 | * | 1/1981 |
| GB | 1400033 | | 7/1989 |

OTHER PUBLICATIONS

Bel–Art Products, Inc. Catalogue 198, pp. 362–367.

* cited by examiner

*Primary Examiner*—Aaron J. Lewis
*Assistant Examiner*—Linh Truong
(74) *Attorney, Agent, or Firm*—Lawrence G. Fridman

(57) ABSTRACT

The invention provides a leakproof sealing system for an eyewash delivery apparatus that extends shelf life of sterile or preserved irrigant solution and is tamper evident. The sealing system has a cap that is positioned over an eye-cup. The boss extends from the cap and surrounds a plurality of spray nozzles. The seal is located adjacent the spray nozzles and is compressively held against the nozzles by a plurality of arms situated within the boss.

13 Claims, 3 Drawing Sheets

PERSONAL EYEWASH DELIVERY APPARATUS WITH INTEGRAL LEAKPROOF SEALING SYSTEM

FIELD OF THE INVENTION

This invention relates to an eyewash dispensing apparatus for providing emergency liquid irrigation to an eye. More specifically, the invention relates to a sealing system for an eyewash delivery apparatus that provides a clean sterile and aseptic environment and is tamper evident.

BACKGROUND OF THE INVENTION

In the USA, federal regulations, such as regulations of the Occupational Safety and Health Agency (OSHA) stipulate that where the eyes of a person may be exposed to injurious, corrosive materials, suitable facilities for rapid irrigation or flushing of the eyes or body should be provided. An eyewash system must be within the work area for immediate emergency use. In addition to the OSHA regulations, the eyewash systems have to meet other standards, such as for example, the ANSI standards which are typically applicable to those systems connected directly to a building plumbing network. According to the ANSI standards, eyewash systems must be capable of delivering 0.4 gallons per minute of irrigation liquid for 15 minutes of continuous use. These eyewash systems must also permit the user to hold both eyelids open while flushing both eyes simultaneously. Known portable or personal eyewash systems do not usually meet these standards. Such systems are typically intended to deliver initial or supplemental first aid in the absence of a readily available plumbed eyewash facility. Portable eyewash systems are often used until further emergency medical treatment can be provided on site or are used on route to a local hospital. The ANSI standard recommends the use of a preserved, buffered saline solution in all emergency eyewash devices, both self-contained and directly plumbed.

Emergency eyewash devices for dispensing liquids to the eye are in wide use in factories and other industrial installations where the danger of injury to the eye exists due to splashing of chemicals, dust, dirt, metal filings and other irritants which may be present. One type of prior art device has generally included a resilient container filled with liquid, a simple threaded closure encapsulated in a heat shrink tamper evident seal or a tamper evident band located between the closure and container. Another type of prior art device is in the form of an empty squeezeable container, and adapter for the eye, such as an eye-cup and a cover for the eye-cup, such as a cap. The container, eye-cup and cap are formed without an integral sealing system. In this instance, the container must be filled separately and refilled every few months to minimize contamination. A further type of prior art device is in the form of a filled squeezeable container, an adapter for the eye, such as an eye-cup and a cover for the eye-cup, such as a cap. The container, eye-cup and cap are formed without an integral sealing system. This type of eyewash device is subject to leaks developed during shipping and handling. To minimize contamination it also has to be constantly refilled.

One such prior art device is disclosed by U.S. Pat. No. 3,917,119 to Kahn. The contents of which are specifically herein incorporated by reference. Upon squeezing the container, the liquid is forced through the tube to the eye cup for irrigating, rinsing, flushing, cleaning or otherwise relieving the eye of the irritant. The prior art devices, while performing the function of flushing the eye with liquid, are disadvantageous in that they are difficult to liquid seal in an clean or aseptic manner that is tamper evident. It is important that the liquid applied to the eye be in a sterile condition. The seal on an emergency eyewash device should keep the liquid contents in a sterile or preserved condition during long periods of storage before use. Further, any sealing device must be quickly and readily removable because any delay in the application of the irrigation liquid may result in additional damage to the affected tissues in the eye. In an emergency situation any delay in applying the eyewash liquid to the eye is detrimental to the health of the user.

Thus, it is an object of the invention to provide a personal eyewash delivery apparatus having a dual sealing system which is leak proof during shipping and handling. Another object of the invention is to provide an eyewash apparatus having one step removal of an internal and external sealing arrangements. It is a further object of the invention to provide an eyewash apparatus with the sealing system having improved shelf life for both sterile and preserved eyewash irrigation fluids.

SUMMARY OF THE INVENTION

The present invention provides a sealing system for an eyewash delivery apparatus that is sterile or aseptic and tamper evident. One aspect of the present invention provides a seal for an eyewash apparatus that is operated by a user. The eyewash apparatus has a fluid reservoir, an eye-cup attached to the fluid reservoir and an irrigation liquid contained within the fluid reservoir. A cap that is located over and in surrounding relationship to the eye-cup. A seal or gasket is located between the cap and the eye-cup to seal the irrigation liquid within the eyewash apparatus. A pull tab is attached to the cap and extends outwardly. The pull tab removes the cap from the eye-cup when actuated by the user. Another aspect of the present invention provides for several spray nozzles that are located within the eye-cup. The spray nozzles are in communication with the fluid reservoir.

Still another aspect of the present invention provides for a drain tube which passes through the eye-cup. The pull tab having a plug that extends into the drain tube to seal the drain tube and to keep the irrigation liquid within the eye-cup. The plug is removed from the drain tube when the pull tab is actuated by the user.

A further aspect of the present invention provides a conforming cover that extends over the cap and the eye-cup. The conforming cover partially covers the pull tab and is readily removable when the pull tab is actuated by the user. The conforming cover is perforated to allow for easy removal by the user and is formed from a shrink wrap material.

Still further aspect of the present invention provides an outer rim associated with the cap for holding the cap to the eye-cup.

The cup and seal are removed by the user by pulling outwardly and upwardly on the grasping portion of the pull tab. As the pull tab is pulled, it breaks through the parallel perforations of the shrink wrap material. As the user continues to pull on the pull tab, the pull tab is bent upwardly and a plug is removed from the drain tube. The plug prevents any irrigation fluid that may have entered the eye-cup from leaking during storage. As the user continues to lift on the pull tab, the lip is pulled away from the eye-cup upper end resulting in the cap moving above the eye-cup. At the same time, the gasket is removed from the spray nozzles and the boss slides away from the discharge end. The user continues to lift on the seal until both the cap and the shrink wrap material are removed from the eye-cup. The eyewash apparatus is now exposed and ready to use.

The design of the present invention provides for an easy to manufacture leakproof seal that has improved performance. The seal prevents irrigation fluid from exiting the eyewash apparatus. The seal maintains the eye-cup and irrigation fluid in a clean, sterile and aseptic condition. The seal serves as a prevention device against any tampering that may be attempted on the eyewash apparatus. Any breaks in the shrink wrap material are indicative of possible tampering. The seal's ability to be rapidly removed does not impede its use during an emergency.

Further features and advantages of the present invention will appear more clearly on a reading of the detailed description of the preferred embodiment of the present invention, which is given below with reference to the accompanying drawings.

DESCRIPTION OF THE PREFERRED EMBODIMENT

While the present invention will be described more fully hereinafter with reference to the accompanying drawings, in which particular embodiments are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1:
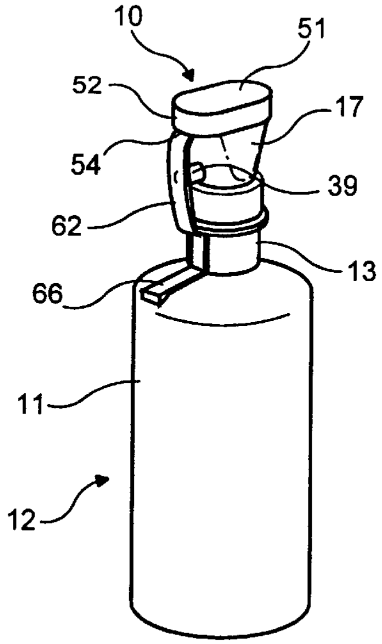
FIG. 1 is a perspective view of an eyewash apparatus with an integral leakproof sealing system of the invention.
Figure 2:
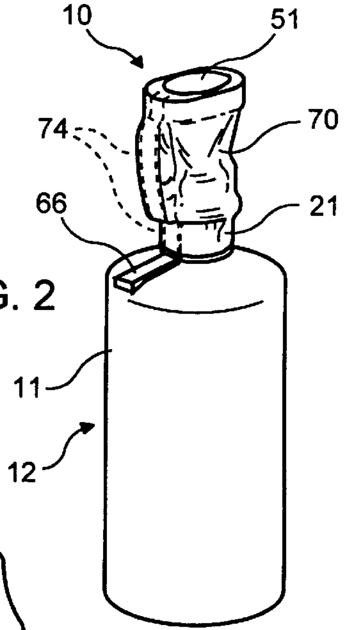
FIG. 2 is a perspective view of the eyewash apparatus with a conforming cover applied.

Referring to FIGS. 1 and 2, a perspective view of an eyewash apparatus with an integral leakproof sealing system is shown. The eyewash apparatus consists substantially of a container or fluid reservoir 12, an eye-cup assembly 7 and a leakproof sealing arrangement 10. The container 12 is formed with a main body 11 and a neck portion 13 having an outside periphery which is substantially smaller than an outside periphery of the main body. A restricting member or rib 14 extends outwardly from outside periphery of the neck portion. The restricting member is positioned on the neck portion remotely from the main body so as to define a sealing zone 21 between the restricting member and the main body. The neck portion 13 is adapted for mutual engagement with an eye-cup assembly 7. In use, the container or fluid reservoir 12 holds an irrigation liquid 9 which is preferably a preserved or sterile, buffered, saline solution. Container 12 can be economically fabricated by conventional molding methods from a suitable resilient plastic such as polyethylene or some other similar material. If desired, it may have shapes other then cylindrical. For example the container can have square or triangular outside periphery.

Figure 5:
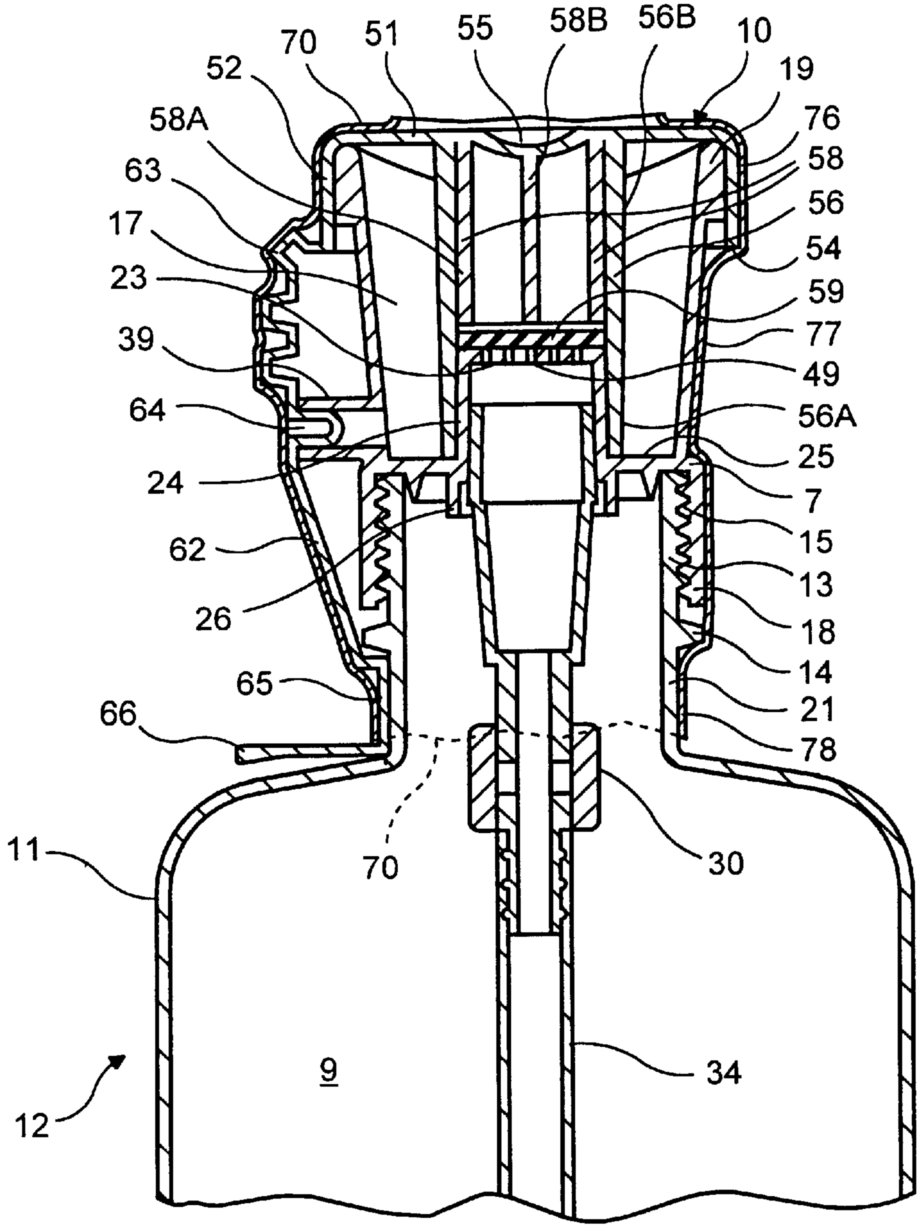
FIG. 5 is a cross-sectional view showing details of the eyewash apparatus and the sealing system in a sealed condition.
Figure 6:
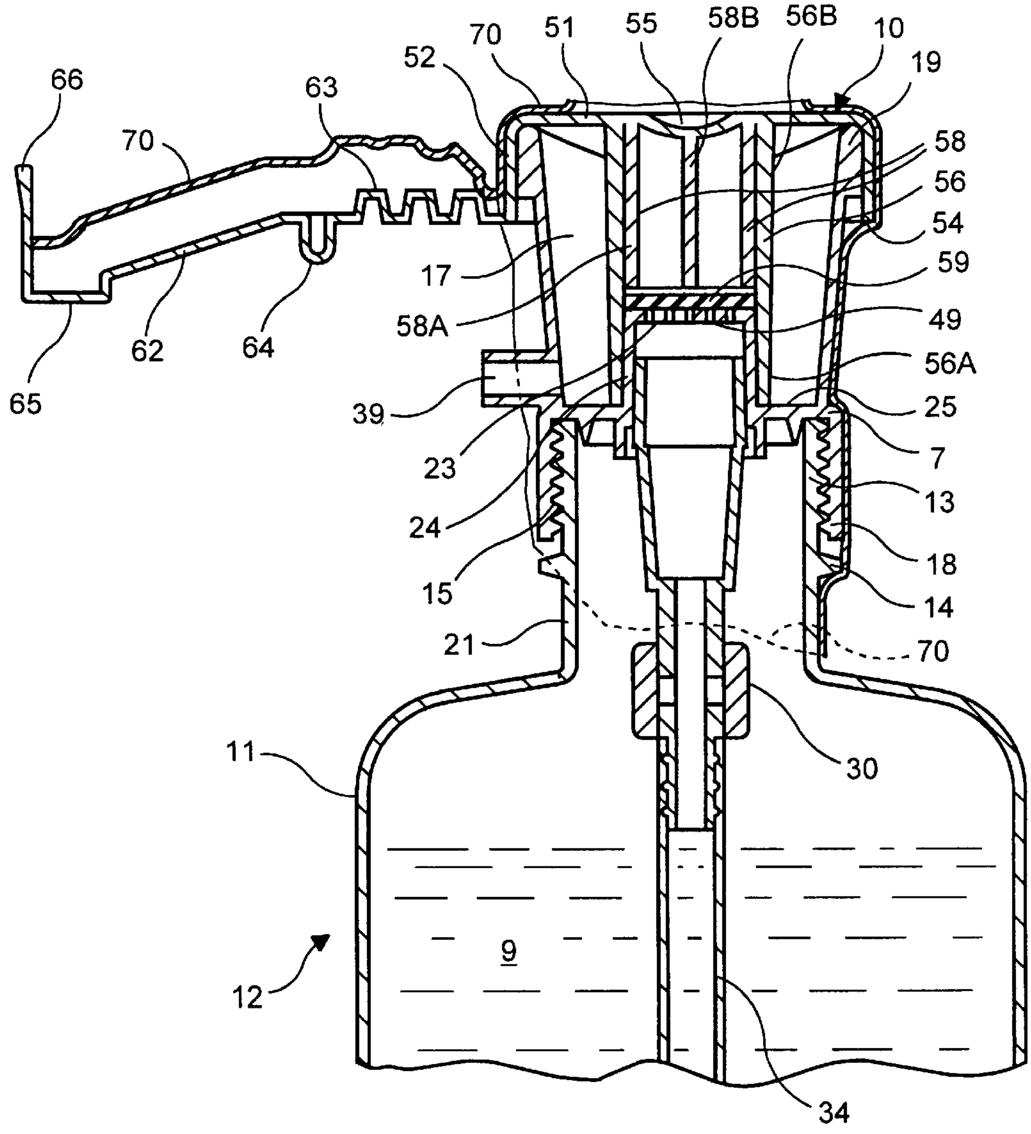
FIG. 6 is a cross-sectional view showing details of the eyewash apparatus and the sealing system after a pull tab is lifted.

Referring to FIGS. 5 and 6, a cross-sectional view of the eyewash apparatus and sealing system is shown detailing additional features of the invention. The eye-cup assembly 7 extends between a substantially hollow eye-cup receiving member 17 formed with an engaging flange 19 at the top and a substantially cylindrical connecting portion 18 at the bottom. The eye-cup 17 by means of engaging flange 19 is designed to make a contact with and to be placed over an eye socket surrounding the eye of a user that is desired to be irrigated. An inner area of the hollow eye-cup receiving member 17 is separated from an interior of the connecting portion 18 by a wall 25. A spraying tubular element 24 extends within the receiving member from the wall 25 in the direction of the engaging flange 19 and is formed with a discharge end 23 and an inlet end 24. The discharge end 23 of the tubular element 24 is formed with a plurality of fluid spray nozzles 49 providing communication between the fluid container 12 and the inner area of the hollow eye-cup receiving member 17. The inner area of the spraying tubular element 24 is in direct communication with the container or fluid reservoir 12 and is adapted to closely receive a tube 34 extending through the irrigation liquid 9. The eye-cup assembly and tube 34 are also made of a conventional plastic by molding and extrusion methods, respectively.

Any conventional means of engagement between the connecting portion 18 and neck portion 13 of the container is contemplated. However, in the embodiment illustrated in FIGS. 5 and 6 connecting portion 18 carries a plurality of internal threads and neck portion 13 carries a plurality of external threads. Such threads are designated by the numeral 15. The threads 15 of the neck portion 13 and connecting portion 18 are in screw-thread engagement when the eye-cup 17 is placed over the neck of the container and rotated. This secures the eye-cup assembly 7 to container 12 and closes the fluid reservoir. In the assembled condition of the invention, the lower part of the connecting portion 18 is positioned in the vicinity of the restricting rib or member 14.

A gravity actuated movable slide valve 30 is provided within the tube 34. The operation of slide valve 30 is described in detail in U.S. Pat. No. 3,917,119. Slide valve 30 allows for the greatest amount of irrigation liquid to be delivered to the eye regardless of whether the container is above or below the eye or whether the container is in an upright or in an inverted position.

The discharge end 23 of tubular member 24 contains a multiplicity of fluid spray nozzles 49 providing fluid communication between eye-cup 17 and container 12. Nozzles 49 serve the purpose of breaking up the pressurized stream of irrigation liquid 9 effected upon squeezing container 12. This enables the invention to facilitate gentle dispensing of liquid 9 to the eye or any other organ which is desired to be irrigated. The wall 25, among other functions, facilitates and prevents an uncontrollable stream of liquid from the container to the eye cup upon tilting or inverting the container and facilitates gentle dispensing of irrigation liquid.

A drain tube 39 provides fluid communication between the eye-cup 17 and outside environment and is adapted for discharging used irrigation liquid 9. Drain tube 39 is positioned in direct vicinity of the wall 25 and extends outwardly from eye-cup 17.

Leakproof sealing arrangement 10 includes an oblong cap 51 which is adapted to be mounted over the engaging flange 19 of eye-cup 17. Cap 51 is formed with an outer rim 52 having a bottom edge 54 which surrounds or fits over the exterior of the engaging flange 19. A central curved or recessed portion 55 is provided on an inner surface of the cap 51. A substantially cylindrical boss 56 extends outwardly from the central area of cap 51 in such a manner that its cap end 56B is connected to cap 51 and a seal end 56A is positioned remotely therefrom. To facilitate in proper positioning and aligning the cap over the eye-cup, in the assembled condition, the interior of the boss 56 in general, and its seal end 56A in particular, are situated in the closed vicinity of the tubular member 24. A multiplicity of arms 58 each having a first or gasket end 58A and a second end 58B are located within the inner area of the boss 56. The arms 58 are typically separated from each other and spaced along the inner periphery of the boss 56. Although FIGS. 5 and 6 show that the arms 58 are formed integrally with the cap 51, an embodiment in which the arms are independent from the cap is also contemplated by the invention.

A resilient seal or gasket 59, typically made of elastomeric material with a stiff plastic backing, is interposed between the gasket ends 58A of the arms and the discharge end 23 of the tubular member 24. Thus, in the assembled condition, the seal 59 is positioned over discharge end 23 to cover the nozzles 49 of the tubular member 24. Upon positioning of the cap 51 on the eye-cup 17, the inner surface of the cup including the outer rim 52 engage the flange 19. The seal or gasket 59 is retained in a compressed state against discharge end 23 by the gasket ends 58 A of the arms 58. Since the seal or gasket 59 is compressed over the discharged end 23, it seals the nozzles 49 and prevents irrigation liquid 9 from escaping. This arrangement is especially effective in preventing leakage when the eyewash apparatus is positioned upside down or sideways during shipment. The combination of the arms 58 and seal 59 is the primary liquid sealing mechanism for the eyewash apparatus of the invention.

Attached to the bottom edge area 54 of the outer rim 52 is a flexible pull tab 62 having a grasping portion 66 at one end thereof. To facilitate bending of the pull tab, especially when it is lifted upwardly, as can be best seen in FIG. 6, a pleated shaped section 63 is provided at the edge 54 of the cap 51. A plug 64 adapted for engagement with overflow tube 39 is situated on the pull tab near the pleated section 63. In operation, when the tube 39 is unobstructed, the fluid 9 after being sprayed through the nozzles 49 is not accumulated within the eye-cup 17, but is discharged through the tube. This prevents reentrance of the used fluid into the container and prevents contamination of its content. While in storage or in transportation, when the tube 39 is closed by plug 64, this arrangement prevents any irrigation fluid 9 that may have entered eye-cup 17 through nozzle 49 from leaking outside of eye-cup 17. At the plug 64, pull tab 62 bends inwardly to form a section 65 which in the assembled condition is adjacent to the sealing zone 21 of the neck portion 13. From section 65, the pull tab 62 projects outwardly to define a grasping portion 66 designed for easy holding by a user. The cap and pull tab 62 are made of a suitable injection molded plastic such as polyethylene or some other similar material.

A conforming cover 70 of plastic shrink wrap material is applied over and covers cap 51, eye-cup assembly 7, neck portion 13 and pull tab 62. The cover 70 also serves as a secondary liquid sealing mechanism for the eyewash apparatus and can be conventionally affixed in place by heating. In the assembled condition, the grasping portion 66 extends outwardly from and is not covered by the conforming cover 70.

To facilitate removal of the conforming cover 70 it is formed with at least a pair of substantially parallel lines of perforations 74 extending generally along the length of pull tab 62. It is desirable that one of the lines of perforations 74 is located on each side of pull tab 62.

In this manner, the conforming cover 70 forms at least top 76, intermediate 77 and bottom 78 engaging portions. The top portion 76 covers at least the cap 51 and the intermediate portion 77 closely engages at least a portion of the eye-cup. The bottom portion 78 of the conforming cover engages at least the sealing zone 21 of the neck portion preventing disengagement between the cap and the eye-cup and retaining pressure compressing said gasket against said eye-cup.

Figure 3:
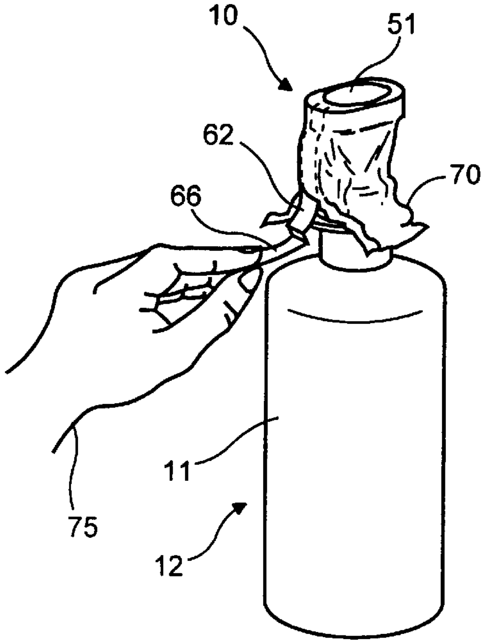
FIG. 3 is a perspective view showing a user pulling a pull tab to start removal of the sealing system.
Figure 4:
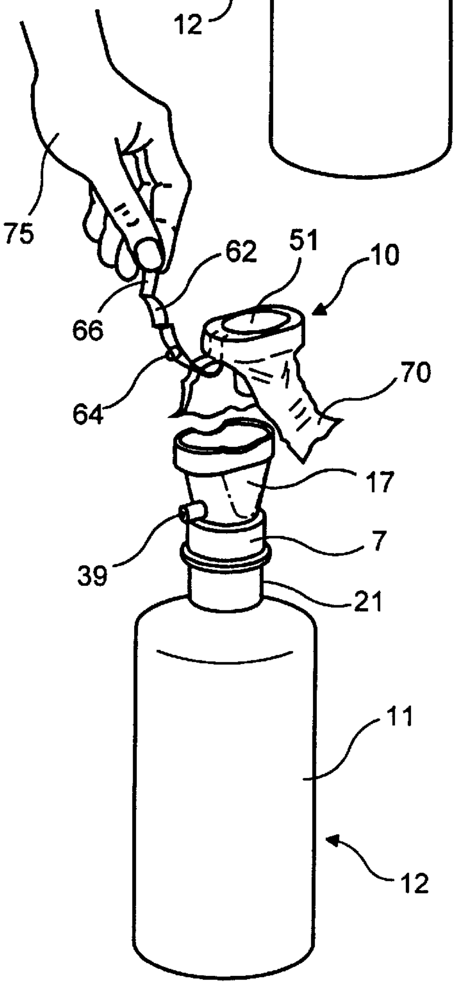
FIG. 4 is a perspective view showing the sealing system in a further state of removal with the seal removed and ready for use.

Referring to FIGS. 3 and 4, a perspective view of the eyewash apparatus is shown with a user removing the sealing system. A hand 75 of a user is shown holding grasping portion 66 of the pull tab. The leakproof seal arrangement 10 including the cap 51 are removed by pulling outwardly and upwardly on grasping portion 66. As pull tab 66 is pulled, it breaks through the parallel perforations 74 of the shrink wrap material. As the user continues to pull on the pull tab 62, it is bent upwardly and a plug 64 is removed from its engagement with tube 39. As the user continues to lift on the pull tab 62, outer rim 52 is moved away from flange 19 resulting in cap 51 starting to move outwardly from the eye-cup 17. The boss 56 and arms 58 slide away from discharge end 23 of the tubular member 24, and the gasket 59 is released from its engagement with the spray nozzles 49. The lifting is continued until both the cap 51 and conforming cover 70 are removed from eye-cup 17. The eyewash apparatus is now exposed and ready to use.

The leakproof seal arrangement 10 performs several desirable functions. First, the seal prevents irrigation fluid from exiting the eyewash apparatus. Second, the seal maintains the eye-cup and irrigation fluid in a clean and sterile condition. Third, the seal serves as a prevention device against any tampering that may be attempted on the eyewash apparatus. Any breaks in the shrink wrap material are indicative of possible tampering. Fourth, because the seal is rapidly removable, the removing operation does not delay the use of eyewash apparatus during an emergency.

The eyewash apparatus with an integral leakproof sealing system is assembled in the following manner. Initially, the container 12 is filled with irrigation fluid 9 and the eye-cup assembly 7 having tubular member 24 and tube 34 are placed over neck portion 13. The connecting portion 18 is rotated to engage threads 15 and tightened. Then, cap 51 is placed over the engaging flange 19 and pressed down such that the seal end 56A of the boss is positioned at the discharge end 23. As cap 51 is continued to be pressed down, the seal or gasket 59 is compressed by the ends 58A of the arms 58 against discharge end 23 sealing spray nozzles 49. This enables the invention to retain cap 51 on eye-cup 17 and to keep gasket 59 in a compressed state. Pull tab 62 is moved such that plug 64 is forced into overflow tube 39 and section 65 is adjacent neck portion 13. Grasping portion 66 now projects outwardly from neck portion 13. Next, the shrink wrap material of the conforming cover 70 having perforations 74 is placed over cap 51 and eye-cup assembly 7. Heat is applied to the shrink wrap material causing it to reduce in size or contract completing the assembly.

It will be appreciated that the sealing system according to the invention saves valuable time in an emergency situation in that the seal is readily removable. It can also be seen from the description of the invention that a sealing system has been provided that seals the irrigation liquid within the container and keeps the eyewash apparatus and liquid in a sterile condition during storage and shipment.

The preferred embodiment of the invention showed the use of the outer rim to retain the cap to the eye-cup. It is contemplated to use a perforated plastic ring to retain the cap to the eye-cup, similar to those used on plastic milk jugs. The plastic ring breaks off from the cap when the cap is removed by a user. Threadable engagement between the cap and eye-cup could also be used to retain these elements together.

While there has been described and illustrated embodiments of a specific superior sealing system for an eyewash apparatus that provides an aseptic environment and is tamper evident, it will be apparent to those skilled in the art that variations and modifications are possible without deviating from the broad spirit and principle of the present invention. The present invention shall, therefore, be limited solely by the scope of the claims which are appended hereto.

What is claimed is:

1. A seal arrangement for an eyewash apparatus, the eyewash apparatus including a fluid reservoir, an eye-cup connected to the fluid reservoir and having a drain tube extending outwardly therefrom, the seal arrangement comprising:

a protective cap adaptable to be positioned over and in surrounding relationship to the eye-cup; and a pull tab associated with the protective cap, the pull tab having a plug adapted to extend into and to seal the drain tube, the plug being withdrawn from the drain tube when the protective cap is removed from the eye-cup during activation of the pull tab.

2. An eyewash dispensing apparatus, comprising:

a fluid reservoir;

an eye-cup connected to the fluid reservoir, the eye-cup having a drain tube extending outwardly therefrom;

a protective cap adaptable to be located over and in surrounding relationship to the eye-cup; and a pull tab associated with the protective cap, the pull tab having a plug adapted to extend into and to seal the drain tube, the plug being withdrawn from the drain tube when the protective cap is removed from the eye-cup during activation of the pull tab.

3. The eyewash dispensing apparatus according to claim 2, further comprising:

at least one spraying nozzle in fluid communication with the fluid reservoir and located within the eye-cup;

a boss associated with the protective cap and extending outwardly therefrom in the direction of the spray nozzle; and a flexible seal located between the boss and the spray nozzle.

4. The seal arrangement according to claim 2, further comprising a conforming cover extending over the protective cap, so as to cover at least partially the pull tab, the conforming cover is formed with perforations to facilitate its removal when the pull tab is actuated.

5. The eye-wash dispensing apparatus according to claim 3, wherein a plurality of arms is located within an interior of the boss, so that in an assembled condition of the apparatus to facilitate a proper positioning of the protective cap over the eye-cup the interior of the boss is situated in a close vicinity of said at least one spraying nozzle and said seal is retained in a compressed state against said at least one spraying nozzle by said plurality of arms.

6. The eye-wash dispensing apparatus according to claim 5, wherein said eye-cup is formed with a tubular member extending between an inlet end and a discharge end thereof, so that said inlet end is in fluid communication with the reservoir, and said at least one nozzle is provided at the discharge end.

7. The eyewash dispensing apparatus according to claim 2, wherein a conforming cover extends over the protective cap, so as to cover at least partially the pull tab, the conforming cover is formed with perforations to facilitate its removal when the pull tab is actuated.

8. An eyewash dispensing apparatus—an external tamper evident conforming cover combination, comprising:

an eyewash apparatus consisting of a fluid reservoir, an eye-cup connected to the reservoir and a protective cap positioned over in surrounding relationship to the eye-cup, at least one spray nozzle in fluid communication with the reservoir and located within the eye-cup, a flexible seal, a boss extending outwardly from the cap, the boss is formed with a plurality of arms located therein, so that upon positioning of the cap on the eye-cup an interior of the boss is situated in a close vicinity of said at least one nozzle and the seal is retained in a compressed state against said at least one nozzle by the plurality of arms; and a conforming cover having at least a top, intermediate and bottom engaging portions, wherein said top portion covers at least said cap and said intermediate portion closely engages at least a portion of the eye-cup.

9. The combination according to claim 8, wherein the eyewash apparatus further comprises the reservoir having a main body and a neck portion having an outside periphery being substantially smaller than an outside periphery of the main body, a restricting member extending outwardly from the outside periphery of the neck portion, said restricting member being positioned remotely from said main body so as to define a sealing zone between said restricting member and the main body; a connecting portion forming a part of the eye-cup and provided for engagement with said neck portion, a free end of said connecting portion being positioned in a direct vicinity of said restricting member, whereas the bottom portion of the conforming cover engages the sealing zone of the neck portion preventing disengagement between the cap and the eye-cup and retaining pressure compressing said flexible seal against said eye-cup.

10. The combination according to claim 8, wherein an outer periphery of the bottom portion of the conforming cover being substantially smaller than an outer periphery of the intermediate portion thereof.

11. The combination according to claim 8, further including a pull tab connected to the protective cap, the pull tab is operable to remove the protective cap from the eye-cup during its actuation, wherein the eye-cup has a drain tube extending outwardly therefrom, the pull tab having a plug adapted to extend into and to seal the drain tube, the plug being removed from the drain tube when the pull tab is actuated.

12. The combination according to claim 11, wherein the conforming cover partially covers the pull tab, the conforming cover is formed with perforations to facilitate its removal when the pull tab is actuated.

13. The combination according to claim 8, wherein the conforming cover is formed from a shrink wrap material.

* * * * *